United States Patent [19]

Woods

[11] 4,422,081
[45] Dec. 20, 1983

[54] VALIDATOR FOR ELECTROCARDIAL DATA PROCESSING SYSTEM

[75] Inventor: Donald C. Woods, Lompoc, Calif.

[73] Assignee: Del Mar Avionics, Irvine, Calif.

[21] Appl. No.: 372,115

[22] Filed: Apr. 27, 1982

Related U.S. Application Data

[60] Division of Ser. No. 88,105, Oct. 24, 1979, which is a continuation-in-part of Ser. No. 957,527, Nov. 3, 1978.

[51] Int. Cl.$^3$ .................. G01D 9/00; G01D 9/28; A61B 5/04
[52] U.S. Cl. .................. 346/33 ME; 346/60; 128/710
[58] Field of Search .......... 346/33 ME, 59, 60; 128/710

[56] References Cited

U.S. PATENT DOCUMENTS

| | | | |
|---|---|---|---|
| 4,006,737 | 2/1977 | Cherry | 128/710 X |
| 4,211,238 | 7/1980 | Shu et al. | 346/33 ME X |
| 4,228,506 | 10/1980 | Ripley et al. | 346/33 ME X |
| 4,346,718 | 8/1982 | Morris | 346/33 ME X |

*Primary Examiner*—George H. Miller, Jr.
*Attorney, Agent, or Firm*—Beehler, Pavitt, Siegemund, Jagger & Martella

[57] ABSTRACT

Apparatus for printing alpha-numeric characters for plotting an incoming signal at rates on the order of one page every seven seconds for rapidly verifying that the system producing the incoming signal is operating properly. Both printing and plotting are done by styli mounted on a moving carriage and individually electrified to produce marks on a specially prepared paper. The stylii are moved back and forth across the paper, marking in both directions. The carriage is not stepped across the page, but instead is moved smoothly from one side to the other side under control of a velocity servo. A controller generates and applies velocity command inputs to the servo, based on the position of the carriage as sensed by an optical encoder, and based on certain characteristics of the incoming signal. A first buffer memory accumulates the incoming signal until a line has been stored for plotting, while a second buffer memory is applying its accumulated contents to the printhead. Thereafter, the first memory supplies the printhead while the second memory accumulates. The apparatus includes a versatile formatting system which determines the amount of data to be plotted in each line in accordance with the incoming timing signals associated with the data. If the timing signals are not present, the apparatus makes the determination autonomously.

23 Claims, 9 Drawing Figures

MODEL 685 DYNAMIC ELECTROCARDIOVALIDATER $^{TM}$

NAME ............ = VISICHIO
REPORT NO. ..... = 3456
AGE ............. = 50
TEST DATE ...... = 5-21-78
SEX ............. = MALE
PHYSICIAN ...... = DR. BIRD DOG
START TIME ..... = 10:03PM
MEDICATION ..... = 5ML PROPANOL

COPYRIGHT 1978  DEL MAR AVIONICS

FIG. 1

MODEL 685 DYNAMIC ELECTROCARDIOVALIDATER ™

NAME............= VISICHIO
REPORT NO....= 3456
AGE............= 50
TEST DATE....= 5-21-78
SEX............= MALE
PHYSICIAN....= DR. BIRD DOG
START TIME...= 10:03PM
MEDICATION...= 5ML PROPANOL

COPYRIGHT 1978    DEL MAR AVIONICS

VALIDATOR FOR ELECTROCARDIAL DATA PROCESSING SYSTEM

RELATED APPLICATIONS

This is a division of application Ser. No. 088,105, filed Oct. 24, 1979, which in turn is a continuation-in-part of application Ser. No. 957,527, filed Nov. 3, 1978.

BACKGROUND OF THE INVENTION

1. Field of the Invention

The present invention is in the field of medical electronics and more specifically relates to a high-speed online printer/plotter for use in validating the operation of an electrocardiographic data processing system.

2. The Prior Art

In the field of electrocardiology it is known that there are advantages to be able to accrue long term ECG data from a patient while the latter is engaged in normal day-to-day activities. While a "resting" ECG, taken while the patient is in a relaxed state and in a supine position, is useful, there are transient conditions of heart abnormality that occur at non-predicatable and infrequent intervals.

Thus, a patient with a suspected heart problem is monitored for a relatively long period, e.g. 24 to 26 hours or longer by a recorder, carried by the patient, and which records the patient's ECG. The recorder is worn by the patient and may record the ECG on a single track of a cassette type magnetic tape or on dual tracks of a reel-to-reel or tape cartridge. The recorder may be of the type which records the ECG in a memory, either in analog or digital form, and may record all beats of the ECG, or periodic time increments of the ECG, or only that portion of the ECG in which an event of cardiac significance occurs as detected by the patient or by the recorder. One such recorder is that described in U.S. Pat. No. Re. 29,921 and which also provides for the patient to place a code on the tape if the patient should experience some event.

After the monitoring period, the usual practice is to analyze the recorded ECG tape by some form of scanner which in effect "reads" the tape or the stored ECG to extract select meaningful data therefrom. Typical scanners are those described in U.S. Pat. No. 4,006,737 and U.S. Pat. No. Re. 29,921. As described, these scanners operate at 30, 60 or 120 times real time and in real time. Thus, for example, a 24 hour tape can be scanned in as little as 12 minutes. The data may be presented as a print-out of a variety of information, as described in the above-identified patents.

As disclosed therein, the scanner includes an arrhythmia computer whose function is to provide arrhythmia information which may include the number of premature ventricular contractions (VE) or supraventricular ectopic beats (SVE) or both, based on the number per hour or a cumulative total. Additionally such computers may be arranged to provide an indication when the number of VE's or SVE's, or both, exceed a preselected number.

Such arrhythmia computers may also be provided with various controls to permit inclusion of R wave amplitude or width as a criteria for VE beat analysis, as well as other parameters such a paired beats, prematurity, width and the like.

Regardless of the format of arrhythmia analysis, there are instances, totally unrelated to equipment performance in which beats visually recognizable by a trained technician or a cardiologist as arrhythmic are not detected by the scanning equipment. Since the number of arrhythmic beats in an hour or the number per 100 or 1000 heart beats may be of significance to the cardiologist, accurate recognition of those arrhythmic beats not recognized by the scanners may be of importance.

It is thus desirable to provide a reliable method or system by which the high speed arrhythmia analysis of the scanner may be accurately and quickly verified against the actual ECG so that those arrhythmic beats missed, or the normal beats recognized by the scanner as arrhythmic may be correlated, either on a time basis or number of beats basis or both with what actually is present in the ECG.

It is also known in the art that a row of styli extending across a strip of paper moving perpendicularly to the row of styli can be programmed to print or plot data along the strip. This technique lends itself to high-speed printing or plotting when required and where it is permissible to record the data on a relatively long strip of paper such as might be wound on a spool. However, in many situations such a format is not acceptable. In many situations, it is highly desirable to print or plot the data in rows extending across a page, with successive rows arranged one below the other down the page, which is what the present invention does. It is by no means obvious how a row of printing styli can be programmed to record the data in this format. It would appear to require substantial storage capacity and considerable complexity to format the data and to print or plot it in successive rows arranged one below the other down a page. The present invention embodies a novel solution to this problem.

Known prior art plotters do not include any means for entering identifying data onto the plotted chart through the machine, thereby necessitating a separate operation to write the identifying data onto the plotted page. Particularly in the case of medical records, it is essential that the record be properly identified by the patient's name and it is convenient if other vital statistics of the patient are also printed by the machine onto the record.

In some instances, the data to be plotted is accompanied by intermittent time signals. Typically, the data to be plotted is played back from a tape recording and fed to the plotter. An analog-to-digital converter within the plotter is clocked at a constant frequency to convert the data to digital form at a constant sampling rate. If the playback speed of the tape varies, the time between successive played back time signals will also be variable. Therefore, the number of samples of data stored between successive time signals also will vary with the playback speed. Further complicating the situation is the possibility that the time signals may sometimes be omitted.

Normally, it is desirable that the occurrence of a time signal should mark the end of a plotted row of data on the chart. This could be accomplished by starting a new line each time one of the time signals occurs; but, if one of the time signals fails to occur, a problem will result. This situation has, so far as is known, not been the subject of prior work in the art. The present invention includes provision for situations of this type.

SUMMARY OF THE INVENTION

The present invention accordingly provides an improved method and system for verifying the results of the automatic analysis of ECG data insofar as that analysis relates to arrhythmic events or patient identified events or both.

The methodology which forms the basis for the verification procedure involves providing a record, in the form of a print-out of selected portions of a long term ECG after, or simultaneously with automatic analysis so that arrhythmic events recognized in the analysis may be correlated, by visual examination with the corresponding portion of the ECG data to ascertain the difference, if any, between the two.

As will be appreciated, visual examination of a plot of ECG wave form is principally a pattern recognition process. Trained technicians and cardiologists may well see visually deviations from normal heart beats for a patient, especially those deviations in the form of arrhythmic events. Where the format of the visual presentation is condensed, i.e. compressed in time and presented as a series of parallel line traces across a page, the process of pattern recognition for abnormal beats by the trained specialist is vastly simplified as compared to a real time print-out of the data as may be presented, for example in the trace of "resting" ECG.

In part, the simplicity of the present invention derives from the fact that relatively short portions, e.g. 30 to 60 seconds, may be printed out or sequentially printed out, so that precise selected regions of the original ECG data may be examined and compared with the automatic analysis of the corresponding portion of the same data as analyzed automatically for arrhythmic events.

Thus the equipment of the present inventions receives various types of inputs. One input is data representing the ECG as taken from the patient. Typically this input is an analog form of the ECG. The second input represents time in the context of the time of day in which the ECG data was originally taken from the patient. It is this time data which permits the necessary correlation of the automatic analysis with patient experience and with the verification of the results of the automatic analysis, all with reference to the actual time of day of the event. Optionally, the input may be data representing those events recognized by the scanner e.g. VE beats and SVE beats as well as patient triggered event signals. The third type of signal are control signals, to be described.

In operation, the apparatus of this invention may continuously print out ECG data in condensed form at a rate far in excess of real time, and at a speed comparable to the speed of the scanner, e.g. 60 to 120 times real time, and presented in a format which promotes visual verification of arrhythmic events and any other noticable abnormality. In this mode, the operator has the option of the portion and the amount to be printed out either during scanner analysis, or after scanner analysis by playing back on the scanner and printing out any selected portion. This may for example be done with reference to the time of day of the original ECG, e.g. going back in the ECG data to those events which took place say at 1:30 A.M. and printing out the data thereafter.

In another mode, print-out for verification may be initiated automatically by an event recognized by the scanner, e.g. VE or SVE beats or, optionally, patient activated events. In this form, each time the scanner recognizes an event, that event signal triggers the print-out so that the portion of the ECG which contains the event, including a segment prior to and subsequent to the event, is printed out each time an event is recognized.

Regardless of the mode, the print-out also provides time of day print-out corresponding to the actual time of day the ECG data printed so that there is precise correlation of cardiac events and time of day.

Also part of the present invention is a high-speed on-line printer/plotter, particularly well adapted for use in plotting electrocardiographic data played back from a magnetic tape. In the present invention, the data is plotted in rows extending across the page, and successive rows are arranged one below the other down the page.

The printing head moves across the page in a continuous uninterrupted motion.

A dual buffer is used, with one memory reading in the incoming data, while the other memory holds the data waiting to be read out for plotting.

In one form of the present invention, the marking head prints back and forth across the page. As disclosed, when the marking head is moving from left to right, the data is read out of a first memory in the same order in which it was read in for storage. When the marking head is moving from right to left, the data to be plotted is read out of the second memory in reverse order from the order in which it was read in. Data is read into the memory for storage at a rate equal to the clock rate of the analog-to-digital converter, but the stored data is read out of the memories in relation to the instantaneous carriage position and at a faster rate than it was read into the memory.

The present invention includes a text memory and a keyboard for entering identifying data and for altering the stored identifying data. This feature is particularly useful in medical applications where it is desired that the patient's identification should appear in permanent form on the record produced. Other patient-related data can, of course, be printed.

The present invention is especially advantageous in situations where the data to be plotted is accompanied by intermittent timing signals, and where it is desirable to begin plotting the data on a new line each time one of the timing signals occurs. The omission of a timing signal would have serious consequences were it not for the provision made in accordance with the present invention for such a contingency.

In accordance with a preferred embodiment of the present invention, if one of the intermittent timing signals is late, owing to a slower than normal playback speed, and there is no assurance that the timing signal will occur at all, the incoming data is stored in a first memory for possible printing at the end of the line being completed, and is simultaneously stored in a second memory for plotting at the beginning of the next line. If the timing signal does occur, but is late, the address generator of the second memory is reset to zero upon the occurrence of the time signal. On the other hand, if the time signal fails to occur, the address generator of the first memory is reset so that the data that was also read into the second memory will be skipped on read out of the first memory. In this manner, there is no possibility that the same data will be plotted twice, yet all of the data will be plotted, before or after the time signal, as appropriate.

The novel features which are believed to be characteristic of the invention, both as to organization and method of operation, together with further objects and advantages thereof, will be better understood from the following description considered in connection with the accompanying drawings, in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a plan view of the first page of a print-out of the type produced by a preferred embodiment of the present invention;

DETAILED DESCRIPTION OF THE PREFERRED EMBODIMENT

Figure 9:
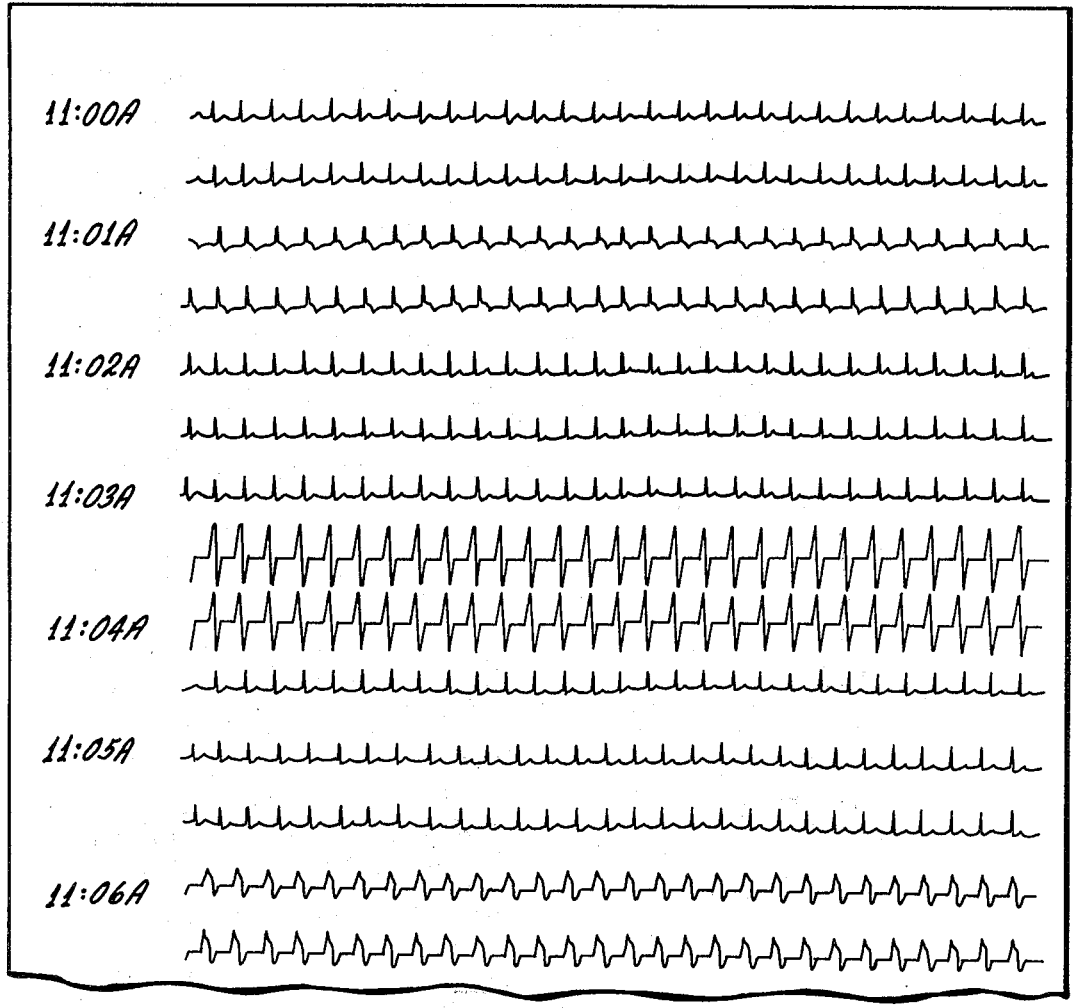

Turning now to the drawings, in which like parts are denoted by the same reference numerals, there is shown in FIGS. 1 and 9 an electrocardiovalidator TM report of the type produced by the apparatus of the present invention. As discussed above, a magnetic tape containing ECG signals recorded at a real-time speed are played back on a playback-analyzer device at a high speed, such as 120 times the real-time speed in the example of FIG. 9. The signals produced by the playback analyzer device are the inputs to the apparatus of the present invention. A signal representing the hour and minute of the day when the ECG signals were recorded may be present on the magnetic tape or alternatively a timing signal may be produced by the playback-analyzer. The purpose of the apparatus of the present invention is to produce a graphic record of the ECG signal at high speeds compatible with those at which the tape is played back. In a preferred embodiment the tape can be played back at either 120 or 60 times the speed at which it was recorded (called the real time speed). Thus, a full 24 hours of real-time ECG record can be plotted by the apparatus of the present invention in only 12 minutes.

FIG. 9 shows the format in which the played back signal is plotted. Each line of the chart represents 30 seconds of real time information and the time signals may be printed down the left margin for each minute, for example. In the form illustrated, the time print-out includes an AM/PM indication as well as the time to the nearest minute. The user of the chart reads the successive lines from left to right. As will be described below, at the ×120 playback speed, the printhead plots the first 30 seconds of each minute of data while moving from left to right to produce the first, third, fifth, etc. lines on the chart, but the printhead plots the second 30 seconds of each minute of data while moving from the right to the left across the page to produce the second, fourth, sixth, etc. lines on the chart. At the ×60 playback speed each of the successive lines of the chart would contain 15 seconds of real time data. As will be seen below, the manner in which the present invention operates prevents the data from being reproduced twice, such as by gaps or overlaps between the end of one line and the beginning of the next line.

In a preferred embodiment, the apparatus of the present invention includes provision for storing and printing the headings such as: "NAME", "REPORT NO", etc. as shown in FIG. 1. In a preferred embodiment the apparatus also includes a keyboard which is used to enter the variable information such as the date, the patient's name, etc. Thus, in the preferred embodiment, a roll of coated paper is inserted into the apparatus, which thereafter produces all of the printing and plotting that appears on the report.

Figure 2:
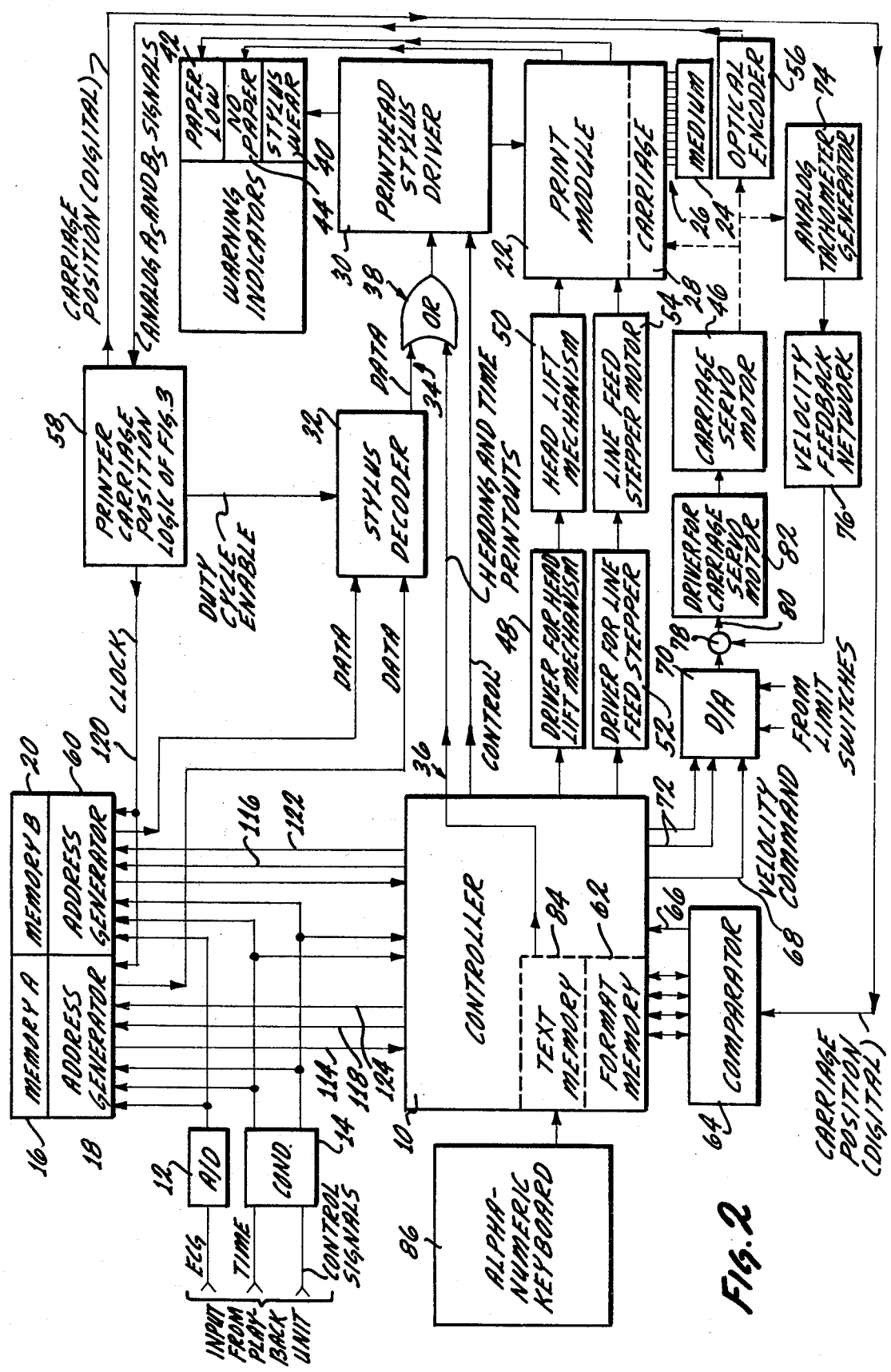
FIG. 2 is a block diagram showing the major components and their interconnections in a preferred embodiment of the present invention.

The block diagram of FIG. 2 shows the major components and their interconnection in a preferred embodiment of the present invention. Three types of signals are received by the apparatus from the playback unit. These include an analog ECG signal, a time signal which is some instances may be absent, and control signals.

The analog ECG signal is converted to digital form by the analog-to-digital converter 12, and the time signal and the control signals are decoded and otherwise, conditioned by the signal conditioner 14. The applied control signals include start and stop signals to initiate and terminate the operation of the apparatus. In a preferred embodiment, the time signals received from the playback unit are parallel binary-coded decimal representations of the hour and minute of the day when the data was recorded, including an a.m./p.m. indicator.

The analog-to-digital converter operates at a rate of 256 conversions per second of real time data, when the playback unit operates at 120 times the real time speed in a preferred embodiment. Accordingly, the conversion frequency of the analog-to-digital converter 12 is 30,720 Hz. At a playback speed of 60 times the real time speed, there are 512 conversions per second and the conversion frequency remains 30,720 Hz.

At the ×120 playback speed, the first 30 seconds of each real time minute of the digitized ECG signal are written into the memory A 16 at storage locations determined by the address generator 18. For purposes of explanation the storage spaces will be regarded as numbered from zero to N, where N is equal to 8K bytes in a preferred embodiment. The storage locations are organized by pages which each hold the data recorded at real time speed in one specond, for the ×120 playback speed (or one half second if the ×60 playback speed is used). Thus, the pages of the memory are numbered 0, 1, 2 ... 29, 30, 31. The data of the first second is stored on the page numbered 0 and likewise, the data of the thirtieth second is stored on the page numbered 29. It is seen that the memories have sufficient capacity to store 32 seconds of data, although typically only 30 seconds of data are stored; the use of the additional storage capacity will be explained below.

When the first 30 seconds of data have been read into the memory A 16, the controller 10 switches the output of the analog-to-digital converter 12 to the memory B 20 wherein the second 30 seconds of each unit of the signal art stored. While data is being read into the memory B 20, the data previously read into the memory A 16 is plotted by the print module 22 onto the medium 24, which in a preferred embodiment is a roll of electro-sensitive pacer, known in the art. Similarly, while the first 30 seconds of the second unit of data is being read into the memory A 16, the second 30 seconds of the first minute of data is being plotted.

In a preferred embodiment, the plotting is done by 32 styli 26 arranged in a column like the teeth of a comb, fixed in position with respect to the carriage 28 to move with it, and having tips which contact the medium 24. In a preferred embodiment, independent, electrical signals can be applied to the styli individually to produce marks on the medium 24 as the carriage 28 moves over it. The carriage 28 is mounted on the print module 22 which includes a track on which the carriage runs back and forth along a path segment which, in a preferred embodiment, is a straight line parallel to the rows of data on the chart of FIG. 1. The styli 26 are arranged in a column which is perpendicular to the path segment, so that if a signal were applied continuously to one of the styli 26, it would trace out a straight line extending across the page. The printhead stylus driver 30 produces electrical signals of the proper magnitude to operate the styli in response to much smaller data signals applied to the printhead stylus drive 30.

During the plotting of an ECG signal, only one of the styli 26 is used at any instant. The stylus decoder 32 receives data to be printed from the memories 16, 20 and determines which one of the styli is to be used to indicate the magnitude of the ECG signal. Thus, at any instant, only one of the lines 34 will be activated. A plurality of lines 36 is provided to permit signals representing alphanumerical printouts to be printed, and in printing such material it may be necessary to activate all of the styli at any one time. The one of the lines 34 associated with a particular stylus and the one of the lines 36 associated with the same stylus are connected to the OR gate 38 so that the particular stylus can be driven by either the ECG data or by the alpha-numeric signals. In a preferred embodiment, one of the styli is shorter than the rest and it provides an indication of stylus wear. The printhead stylus drive 30 then activates a warning indicator 40. Other warning indicators 42, 44 are activated when the supply of paper is low or has been exhausted, respectively.

The carriage 28 is driven back and forth across the page by the carriage servo motor 46; successive lines on the page are plotted in opposite directions of carriage motion. That is, the odd numbered lines are printed as the carriage moves from left to right, and the even-numbered lines are printed while the carriage moves from right to left.

At the end of each line a signal from the controller 10 is applied to a driver circuit 48 which applies power to the head lift mechanism 50 to lift the styli from the paper. While the styli are lifted from the paper, a signal generated by the controller 10 is applied to the line feed stepper driver 52 and causes it to apply power to the line feed stepper motor 54 to advance the paper with respect to the path segment on which the carriage moves.

Movement of the carriage is sensed by an optical encoder 56 which, as will be described below in connection with FIG. 3, generates two sinusoidal signals in quadrature in relation to the rotational position of the shaft of the carriage servo motor 46. These signals are applied to the printer carriage position logic circuit 58, which produces digital signals representing the position of the carriage along the path segment over which it moves. The printer carriage position logic circuit 58 also produces clock pulses in relation to the position of the carriage along the path segment, and these clock pulses are used to increment the address generators 18, 60, to read out the data stored in the memories 16, 20 in relation to the position of the carriage along the path segment.

Thus, successive bytes of data are read into the memories 16, 20 in succession at a rate determined by the analog-to-digital converter 12, but are read out of the memories at a rate dependent on the velocity of the carriage 28 and in such a position related manner that each stored byte is plotted at a predetermined position across the page. In a preferred embodiment of the invention, the stored data is read out of the memories at a faster rate than it is read into the memories. Typically, the entire contents of one of the memories is read out and plotted in less time than is required to read the incoming data into the first 28 pages of the other memory.

The digital carriage position signal generated by the printer carriage position logic 58 is used to control the movement of the carriage 28, as will now described. A velocity feedback servo is used to urge the carriage to move at a commanded velocity, and the velocity that is commanded at any particular time is determined by the controller 10 based on the digital carriage position signal produced by the printed carriage position logic circuit 58.

In accordance with the present invention, certain milestone positions of the carriage along its path segment are defined before the apparatus is put into operation. The milestone positions are stored in a succession in the format memory 62 of the controller 10. A constant velocity command is applied to the velocity servo as the carriage moves from one of the milestone positions to the next; but the velocity command may be altered at each of the milestone positions. The continually changing carriage position is continually compared in the comparator 64 with the next milestone to be attained. When the carriage 28 has reached the milestone, the comparator 64 generates an equality signal on the line 66 which permits the controller 10 to recognize that the milestone has been reached. In response to the equality signal on the line 66, the controller 10 generates a velocity command signal on the line 68 which is then converted to analog form by the digital-to-analog converter 70 for use by the velocity servo.

By way of example, assume the carriage is initially at rest at the beginning of a line. Upon receipt of a start signal the maximum velocity is commanded, and this results in the maximum possible acceleration of the carriage. After the carriage has moved a short distance and is approaching the desired plotting speed, it reaches a milestone position at which the commanded velocity is altered to equal the desired plotting speed. This commanded velocity is then maintained as the carriage moves across the page to plot the ECG data. When the carriage approaches the end of the line being plotted, it reaches another milestone position at which the command velocity is reduced to zero, thereby causing the carriage to decelerate and stop at the end of the line. In a preferred embodiment, the controller 10 can independently generate and apply velocity commands via the line 72. Limit switches at the ends of the path segment mechanically actuated by the carriage 28 are also used in a preferred embodiment to generate velocity commands to prevent damage to the apparatus.

The instantaneous velocity of the carriage is sensed by an analog tachometer generator 74 connected to the shaft of the carriage servo motor 46. The analog tachometer generator 74 generates an analog velocity signal which is modified in the velocity feedback network 76 and then is combined at the summing junction 78 with the analog velocity command. The difference between the latter two quantities is the velocity error signal which is applied via the line 80 to the driver 82 for the carriage servo motor. The driver applies power to the carriage servo motor 46 in accordance with the velocity error signal on the line 80.

The controller 10 further includes a text memory 84 for storing alpha-numerical data which can be entered by use of the keyboard 86. The text memory 84 further includes a counter incremented each time a line has been plotted to provide signals representing the line numbers or time printouts shown at the left hand margin in FIG. 1.

Figure 3:
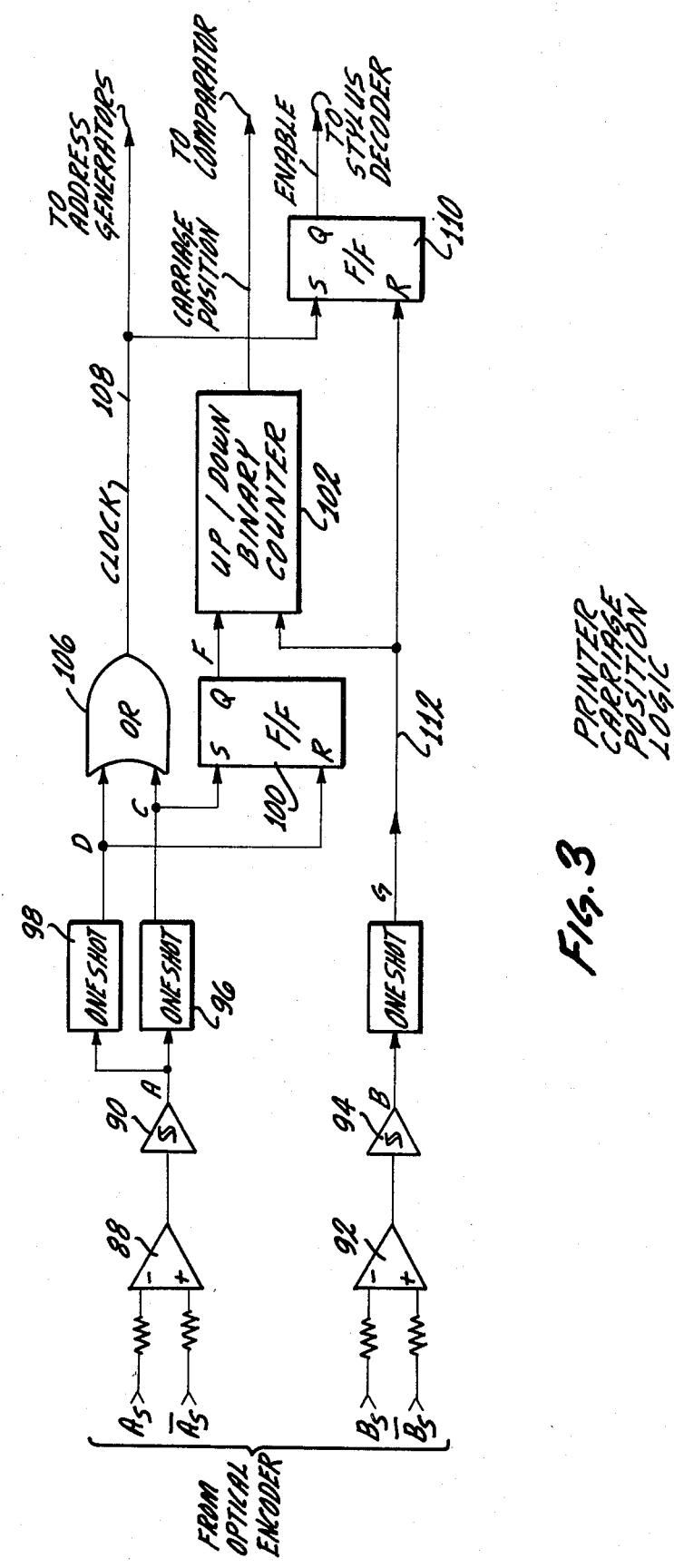
FIG. 3 is a block diagram showing the printer carriage position logic circuit of FIG. 2 in greater detail.
Figure 4:
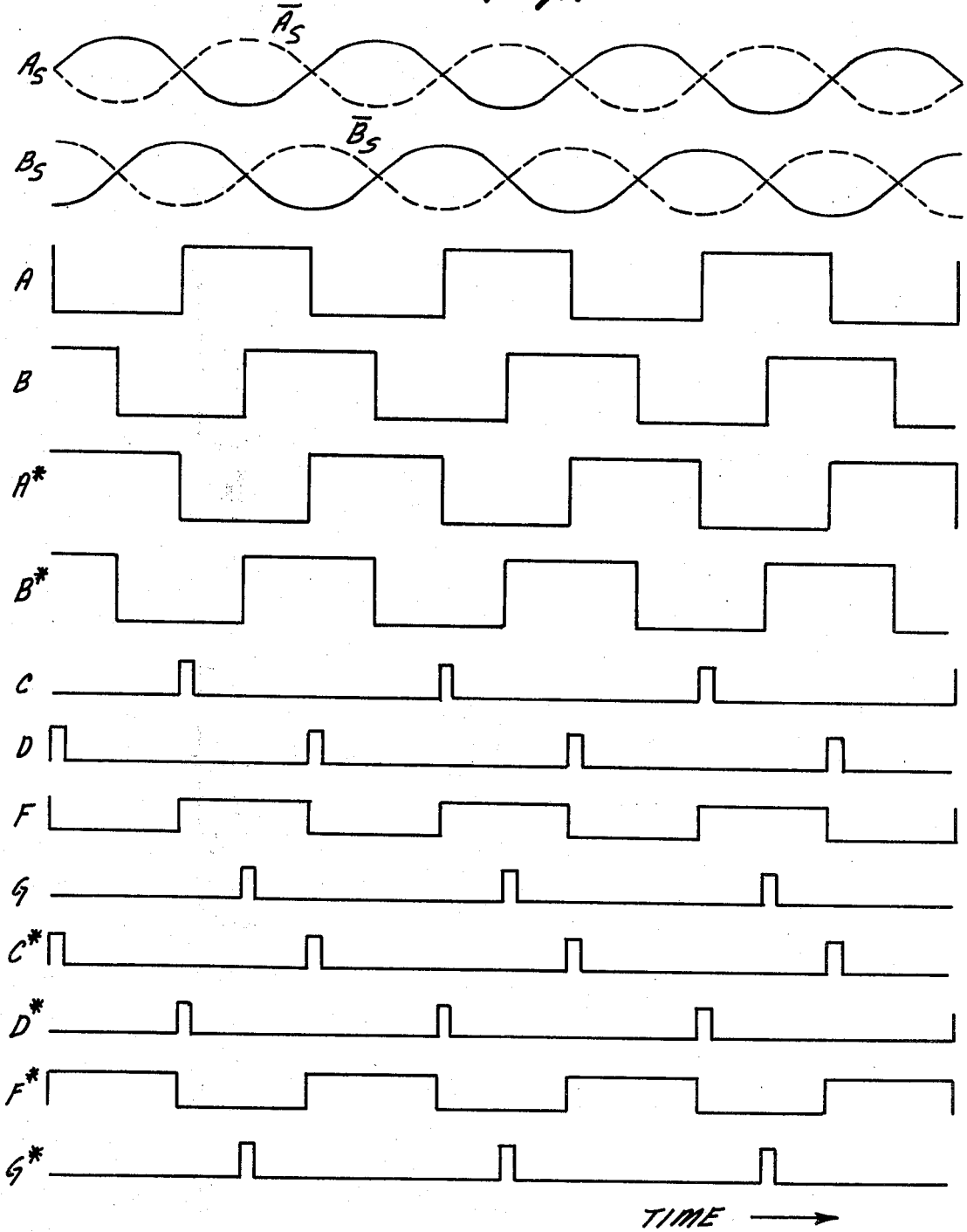
FIG. 4 is a graph showing the time relationship between various signals generated in the printer carriage position logic circuit of FIG. 3.

The printer carriage position logic circuit 58 is shown in greater detail in FIG. 3, and the signals at various points in the circuit are shown in FIG. 4. The optical encoder 56 of FIG. 2 produces the four sinusoidal signals $A_s$, $\overline{A}_s$, $B_s$, and $\overline{B}_s$, which differ from one another by 90 degrees in phase. That is, $A_s$ differs from $\overline{A}_s$ by 180 degrees and $\overline{B}_s$ differs from $B_s$ by 180 degrees. For clockwise rotation, $B_s$ lags $A_s$ by 90 degrees, whereas for counterclockwise rotation $B_s$ leads $A_s$ by 90 degrees. $A_s$ and $\overline{A}_s$ are combined in the operational amplifier 88 and conditioned by the Schmitt trigger 90 to produce the train of pulses which constitute the signal A. Similarly, the signals $B_s$ and $\overline{B}_s$ are combined in the operational amplifier 92 and conditioned by the Schmitt trigger 94 to produce the signal B shown in FIG. 4. The outputs of the Schmitt triggers 90, 94 are the signals A and B of FIG. 4 for clockwise rotation of the optical encoder, and if the rotation is counterclockwise, the output of the Schmitt triggers 90, 94 are the pulse trains A* and B* of FIG. 4.

The output of the Schmitt trigger 90 is applied to the one shots 96, 98 which trigger respectively on the leading and trailing edges of the pulses to produce the signals C and D respectively for clockwise rotation, and C*, D* for counterclockwise rotation. The output of the one shots 96, 98 are used to set and reset a flip-flop 100 to yield the signal F which serves as the up/down control input to the binary counter 102. The output of the up/down binary counter 102 is a digital representation of the instantaneous carriage position.

The signal B is applied to the one-shot 104 which produces the output signal G for clockwise rotation (G* for counterclockwise rotation) which is used by the clock input to the up/down binary counter 102. For clockwise rotation the $\overline{G}$ signal occurs while the $\overline{F}$ signal is high, while for counterclockwise rotation, the G signal occurs while the F signal is low. Thus, the up/down binary counter 102 is incremented during clockwise rotation and decremented during counterclockwise motion.

The signals C and D are also applied to the OR gate 106 to produce a clock signal on the line 108 for use by the address generator which is reading out the data being plotted. The clock signal on the line 108 is used to set the flip-flop 110 which is reset by the signal G on the line 112. The Q output of the flip-flop 110 serves as an enabling signal, in a preferred embodiment, to establish a 50 percent duty cycle for electrical activation of the styli. That is, to operate each of the styli in such a manner that it produces a series of minuscule dots instead of a solid line when continuously operated. In a preferred embodiment, 3,000 clock pulses are produced on the line 108 per revolution of the servo motor, and there are 1300 dots produced per horizontal inch in the graph. Each of these dots is produced by a current pulse of approximately four microseconds duration.

Figure 5:
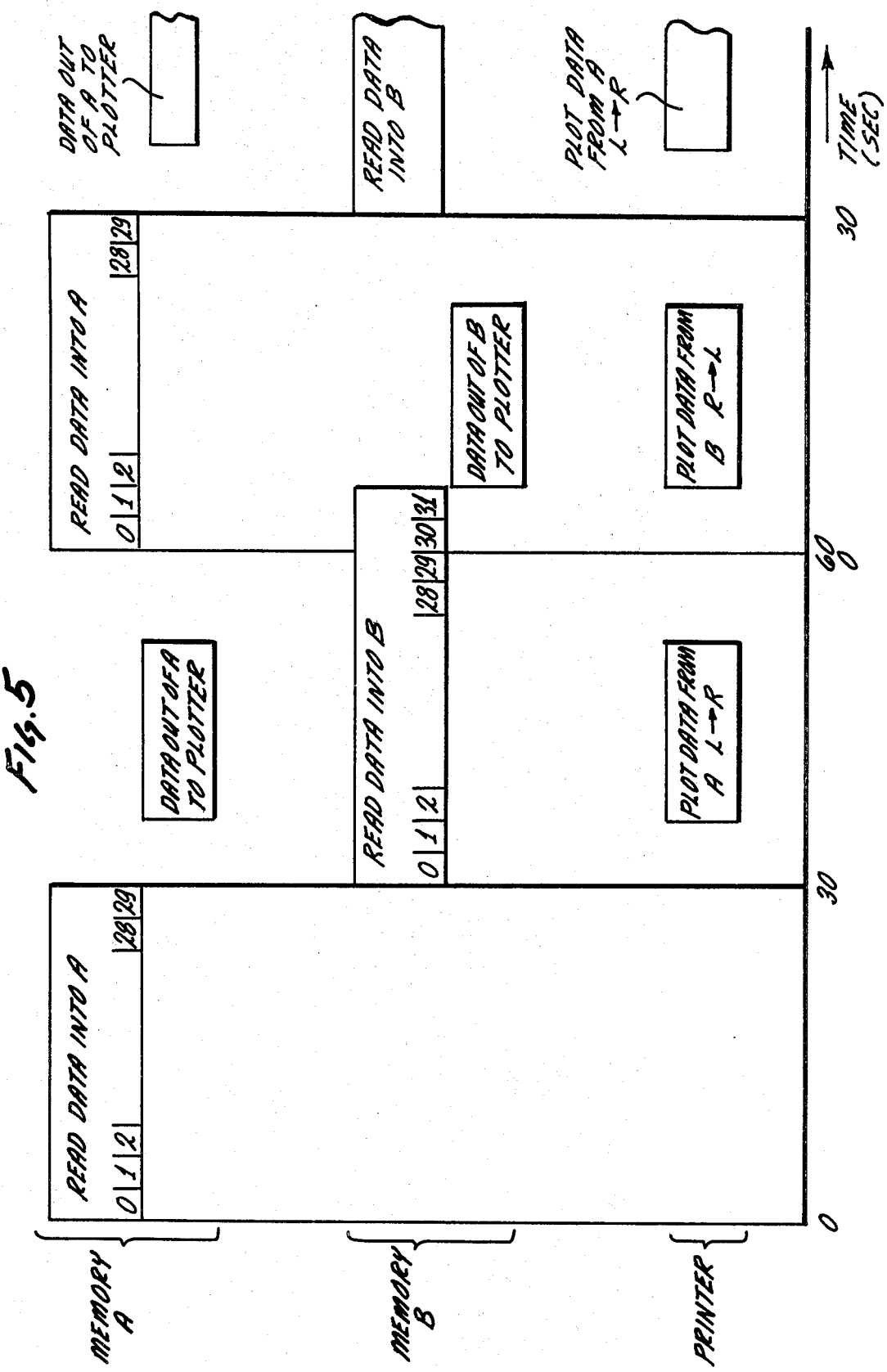
FIG. 5 is a diagram showing the timing of various operations performed by the apparatus of FIG. 2.

The operation of the apparatus of FIG. 2 will now be described by use of the diagrams of FIGS. 5-8. Usually, the patient's name and other data specific to the patient is entered into spaces reserved in the text memory 84 for such information by means of the alpha-numeric keyboard 86. Next, the playback of the recorded tape is begun and control signals from the playback unit serve to indicate to the operator that data is beginning to flow. As indicated in FIG. 5, data played back from the first 30 seconds of real time recording are read into the memory A 16 and stored on pages 0, 1, 2 . . . 28, 29 of the memory. A status signal on the line 114 of FIG. 2 signifies to the controller 10 the number of storage spaces that have been used. In a preferred embodiment, the status signal is simply the instantaneous reading of the address generator 18. When the controller 10 perceives that the last storage space on page 29 of the memory A is filled, the controller switches the stream of incoming data to the memory B 20 by means of a store enable signal on the line 116.

Figure 6:
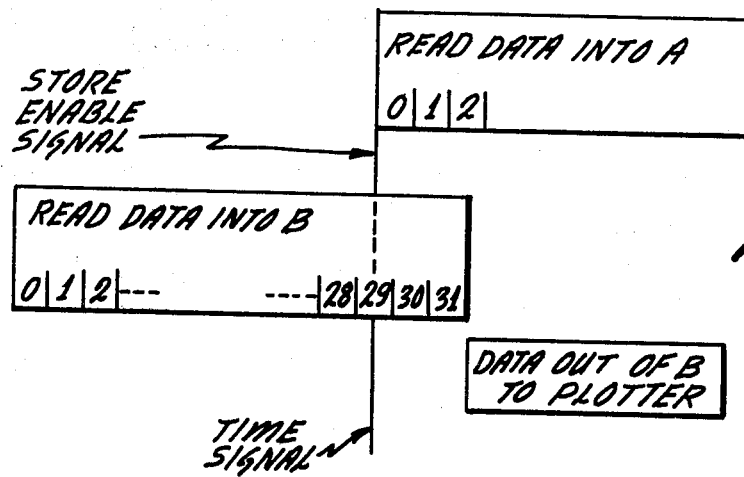
FIG. 6 is a diagram showing the timing of various operations when an incoming timing signal occurs earlier than normal.
Figure 7:
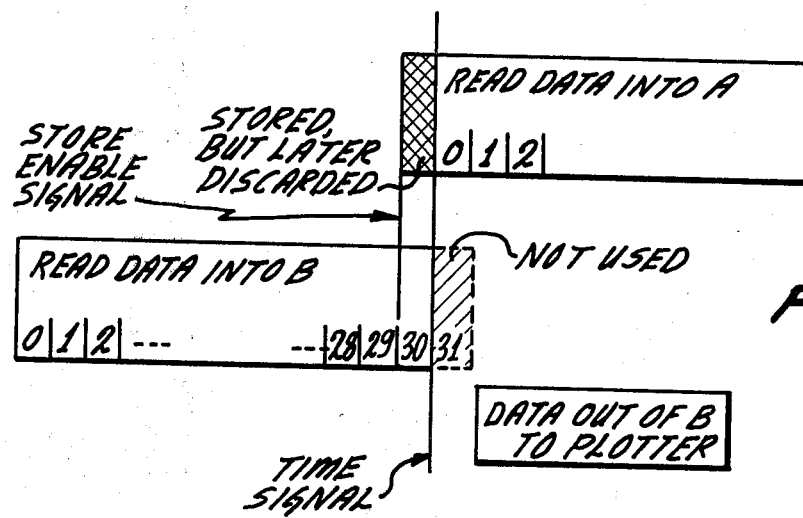
FIG. 7 is a diagram showing the timing of the various operations when an incoming time signal occurs later than normal.
Figure 8:
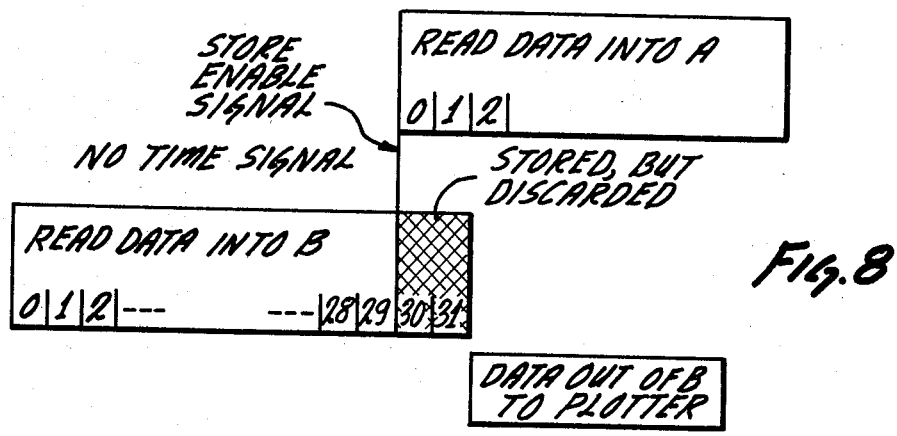
FIG. 8 is a diagram showing the timing of the various operations when an incoming timing signal does not occur; and, FIG. 9 is a plan view of the second page of a printout of the type produced by a preferred embodiment of the present invention.

While the memory A was being loaded, the controller 10 generated a velocity command to get the carriage 28 up to speed and clocked the stored numerical time printout from the text memory 84 to the printhead. This having been done, the controller generates a print enable signal on the line 118 to permit the data stored in the memory A to be read out in relation to the clock pulses produced on the line 120 by the printer carriage position logic circuit 58 of FIG. 2. Thus, the data stored in the memory A is plotted by the carriage as it moves across the path segment from left to right while the data of the second 30 seconds of the first minute of real time recording is being read into the memory B. Likewise, as will be discussed in connection with FIGS. 6, 7 and 8, the data that was read into memory B is plotted by the plotter from right to left across the page in response to a print enable signal generated by the controller 10 on the line 122, while the data arriving in the first 30 seconds of the second minute of real time recording is read into the memory A under control of the store enable signal generated by the controller 10 on the line 124. FIGS. 6-8 show additional aspects of the operation of the apparatus.

In a preferred embodiment, a timing signal is included on the tape being played back and permits an accurate correlation to be established between the data on the tape and the time at which it was recorded. Since the time signal is produced every minute on the minute, it is desirable that the data be plotted on the even numbered lines until the timing signal occurs, and with the occurrence of the timing signal to plot the succeeding data on the next, odd numbered, line.

If the speed of the playback unit varies, or is constant but too fast or slow, it will appear that the timing signal occurs too early or too late relative to the data. In rare situations the timing signal may not appear at all. This situation is handled as illustrated in FIGS. 6-8 in a preferred embodiment of the present invention.

FIG. 6 shows the situation when the timing signal appears to arrive too early in time relative to the data. As indicated in FIG. 6, the timing signal has occurred before the previous page (numbered 29) of memory B has been completely filled. Upon the occurrence of the timing signal before the entire 30th page of the memory B has been filled, the controller 10 generates the store enable signal on the line 124 of FIG. 2 to transfer the incoming data stream into the memory A. There is no gap in the stored data. FIG. 6 shows the situation in which the time signal occurs before the 30th page of the memory B has been completely filled with incoming data. FIG. 7 shows the situation when the time signal occurs "late", that is, after the 30th page of the memory B has been filled with data. Likewise, FIG. 8 shows the situation in which the timing signal does not occur at all.

In a preferred embodiment of the invention, the control means 10 generates the store enable signal on the line 124 when the 30th page of the memory B has been completely filled (as shown in FIGS. 7 and 8), unless the time signal occurs before the 30th page of the memory B has been completely filled, in which case the score enable signal is generated simultaneously with the occurrence of the time signal (as shown in FIG. 6).

As shown in FIG. 7, if the time signal occurs after the 30th page of the memory B has been completely filled, but before the 32nd page of the memory B has been completely filled, upon the occurrence of the time signal the address generator 18 of FIG. 2 is reset to zero. In this case, the store enable signal is indeed generated when the 30th page of the memory B has been filled and at that time, the incoming data is read simultaneously into both memory B and memory A. Thereafter, if the time signal occurs before the 32nd page of the memory B has been completely filled, the controller 10 resets the address generator 18 to zero. Because the address generator 60 reads the stored data out of the memory B in reverse order from the order in which it was read in, it is seen that the data which was stored on the 31st and 32nd pages of the memory B is read out in response to the print enable signal generated by the controller 10 on the line 122. It being recalled that the address generator 18 causes the data stored in the memory A to be read out in the same sequence in which it was recorded, starting with the data stored at the address "zero", it is seen that the data that was stored in the memory A prior to the occurrence of the time signal is never read out and hence is discarded. This mode of operation prevents any part of the incoming data stream from being plotted twice and also assures that all parts of the incoming data are plotted, with no omissions.

FIG. 8 relates to the situation in which the expected time signal does not occur at all, or occurs only after the 32nd page of the memory B has been filled. In this case, as soon as the 30th page of the memory B has been completely filled, the controller 10 generates the store enable signal on the line 124 which results in storage of the incoming data in memory A; however, simultaneously the incoming data is also stored in the memory B, filling the 31st and 32nd pages. If no time signal has occurred by the time the 32nd page of the memory B has been filled, the address generator 18 of the memory A is not reset (in contrast to the situation shown in FIG. 7) but instead, the address generator 60 of the memory B is reset to begin reading the stored data starting with the last entry on the 30th page of memory B (and reading out in reverse order). As in FIG. 7, duplications and omissions are avoided.

In another form of the present invention, the equipment may optionally include an automatic print-out mode triggered by any one of a number of events such as a VE, SVE or patient actuated events. For example, there are recorders which are multiple track tape recorders which on one channel record the ECG and which on another channel or channels may record blood pressure, time of day, patient activated event signals, separately or in addition to the ECG data. In the usual form of multiple channel recorders, as described in U.S. Pat. No. Re 29,921, there are two channels of ECG data and the ECG traces, though of the same heart and at the same time, may not be the same because each channel is from a different set of electrode leads. In that recorder, channel 1 records only ECG data while channel 2 records both ECG data and patient actuated event marks. There are also recorders which will store in memory at predetermined time intervals and for a predetermined length of time ECG data from a patient to store in data response to some recognized cardiac event. The latter type recorders may also store data for some period of time in response to a patient activated command.

There are some scanners, as previously identified, in which the patient data recorded in real time on two channels is scanned at a high speed. Some of these scanners, in addition to scanning at high speed, also include a mode by which upon the recognition of an event, be it a cardiac event or a patient event, reduce scanning speed to real time with an automatic write-out in real time of that portion of the ECG data being processed. These scanners will scan both channels of the tape but the arrhythmia computer operates on only one of those two channels at a time. Thus, the usual procedure involves locating the first arrhythmic event on the tape and comparing that arrhythmic event on each channel to ascertain which of the two channels provides the best signal fidelity i.e. most clearly shows the distorted beat. The channel which provides the best fidelity is then selected for analysis by the arrhythmia computer and is usually channel 1. It is understood, however, that there may be instances in which, for physiological reasons or because of electrode lead placement, or both, channel 2 provides a signal of better fidelity.

As will be apparent, the automatic write-out optional feature of this invention may be used with scanners of the type which recognize events, but with the advantage that the verifying print-out is always at high speed. Where the scanner includes a real time print-out mode triggered by an event, a feed back signal is used to override the scanner speed reduction mode so that both scanning and verification continue at high speed.

Accordingly, the automatic print-out of this invention mode will be explained with reference to a two channel recorder in which channel 1 is the ECG data while channel 2 includes ECG data and patient activated event signals, both recorded in real time.

Thus referring to FIG. 2, the system includes a control board 200 with a three position switch 205 having an "auto" mode, an "off" position and a "validate" mode, as shown. The control board also includes a "reset" switch 207 and a two position channel selection switch 210.

If the scanner includes an automatic real time write-out mode activated by an event, an inhibit signal is fed back through line 211 when switch 205 is in either the "auto" or "validate" mode so that the scanner will operate at its selected speed. In the "off" position of switch 205, the system is in a power on operative status but a "no mode" print-out condition and there is no print-out whatsoever even though data is being received. The mode switch information is fed to signal conditioner 14 through line 212 and to the controller 10 to effect the selected mode of operation.

The ECG data from the scanner is received through line 215 which is actually two separate lines, one for each one channel 1 or 2 of the recorder tape. Since the scanner arrhythmia computer reads only one or the other channel but not both simultaneously, the channel selector switch 210 operates separately from the channel selector switch of the arrhythmia analyzer in the scanner.

From the control panel, the ECG data of the selected channel is fed through line 216 to the A/D converter 12.

The "reset" switch 207 is used to terminate the print-out and return the unit to a heading mode for keyboard entry of patient identification data. Should the "reset" switch be depressed during a print-out operation, the unit will return to a heading mode and the word "Name" will be printed but all data in the text memory 84 will be cleared.

By way of example, if the scanner arrhythmia computer is set for channel 1 and the unit of this invention is set for "validate" and for channel 1, the print-out will continue at 60 or 120 times real time for as long as the scanner operates or until the operator depresses the "reset" button 207. In this mode, the inhibit signal prevents the scanner from going to the real time write-out mode. Should both units be on channel 2 and in the "validate" mode, whatever information which is on channel 2 will be printed out. Since the two channels of recorder tape are simultaneously recording the same physiological event, it is possible to analyze arrhythmic events on one channel in the scanner, but print out the ECG data in the other channel in the validate mode, or to switch back and forth between channels, if there is a reason to do so.

In the auto-write mode, in accordance with this invention, assuming the scanner arrhythmia computer is on channel 1 (where there is only ECG data) and switch 210 of the unit is on channel 1, whenever the scanner recognizes an arrhythmic event, the controller 10 functions to provide the following sequence. ECG data is inputted to one or the other of Memory A or Memory B and there is about a five second overlap in the data stored, i.e. the last five or so seconds (real time) of data stored at the tail end of one memory is also the first five or so seconds (real time) stored at the front of the second memory. Should an event occur, that memory in which the event is first stored is the first read out and printed out. The event signal may be any one of three types, a VE, or an SVE or patient event and enters through line 230 to the signal conditioner and to the controller 10. The occurrence of an event signal triggers the controller to read out that memory in which the event is first stored.

In this way, regardless of the scanner rate, i.e. either 60 or 120 times real time, the print-out portion always includes a segment prior to the event, the event and a segment after the event. In the 60 times mode, the print-out is of 60 seconds real time data; in the 120 times mode, the print out is 30 seconds of real time data. As long as the unit is in the auto-write mode, the sequence continues automatically for each event recognized by the scanner.

It is understood that the system and method of the present invention may take various forms and need not include the sophistication of the auto-write mode. It is, however, important that time of day be presented so that there is a way to correlate the data. For example, it is possible to go back or forward to a specific time on the tape and verify the events with a print-out which identifies timewise when those events occurred. Virtually any portion of the tape may be selected, and the print-out will or should correlate with the time selected.

Thus, there has been described an apparatus for printing out alpha-numeric data and for plotting ECG signals at a high speed to validate the functioning of the ECG recording and playback equipment and to rapidly produce a graphic recording of the ECG data stored on a magnetic tape. The printing is done by a carriage which is moved in a continuous uninterrupted movement back and forth from one side of the page to the other, printing alternate lines in opposite directions. A velocity servo is used to impart the proper speed to the carriage in relation to the position of the carriage along its path. The apparatus is particularly well adapted for use in plotting data accompanied by a timing signal. Data received prior to the timing signal is plotted on a first line, and data received after the occurrence of a timing signal is plotted on the next line. Provision is included for the situation in which the timing signal is absent.

The foregoing detailed description is illustrative of a preferred embodiment of the invention and it is to be understood that additional embodiments will be obvious to those skilled in the art. The embodiment described herein, together with those additional embodiments are considered to be within the scope of the invention.

What is claimed is:

1. Apparatus for controlling the operation of a printer-plotter to produce marks at a high speed on a medium that are representative of electrocardiographic signals generated at a slower real time speed by a patient, then stored in a storage device and later retrieved from the storage device, said apparatus comprising:

formatting means receiving the retrieved electrocardiographic signals and connected to the printer-plotter for controlling it to plot at the high speed successive segments of the retrieved electrocardiographic signals in successive rows juxtaposed along the medium to facilitate visual analysis of the retrieved electrocardiographic signals, said formatting means responsive to applied timing signals to control the printer-plotter to print alpha-numeric symbols adjacent predetermined rows of the plotted electrocardiographic signals to indicate the time of day corresponding to the respective said predetermined rows.

2. The apparatus of claim 1 wherein time of day signals correlated with the electrocardiographic signals and representing the time of day at which the respective electrocardiographic signals were generated have been stored in the storage device along with the electrocardiographic signals and wherein said formatting means further comprise means for retrieving the stored time of day signals for use as the applied timing signals.

3. The apparatus of claim 1 wherein said formatting means retrieve the electrocardiographic signals from the storage device at a speed greater than the speed at which the electrocardiographic signals were entered into the storage device.

4. The apparatus of claim 1 wherein said formatting means control the printer-plotter to plot the successive rows so that they all extend to one side from a common line and to print the alpha-numeric symbols on the opposite side of the common line.

5. The apparatus of claim 1 wherein said storage device includes time-of-day signals corresponding to the time of day when said electrocardiographic signals were stored within said storage device and wherein said formatting means further comprises a first and second memory for storing said electrocardiographic signals and means for controlling the storing of said electrocardiographic signals in said first and second memory wherein said means for controlling simultaneously stores said electrocardiographic signals in said first and second memory for a predetermined period of time during which period said time-of-day signal is to be read from said storage device.

6. The apparatus of claim 5 wherein said means for controlling storage of said electrocardiographic signals in said first and second memories ceases storing said electrocardiographic signals in said second memory and begins to store said electrocardiographic signals in said first memory if said time-of-day signal occurs prior to storage of said electrocardiographic signals in a predetermined address location within said second memory indicative of a predetermined fraction of the storage capacity of said second memory.

7. The apparatus of claim 5 wherein said means for controlling simultaneously stores said electrocardiographic signals in said first and second memory after a first predetermined fraction of the capacity of said second memory has been utilized and if no time-of-day signal is read, discards said electrocardiographic signals stored in said second memory after said first predetermined fraction of said capacity of said second memory.

8. The apparatus of claim 5 wherein said means for controlling stores said electrocardiographic signals in said second memory and simultaneously in said first memory after a first predetermined fraction of said second memory has been utilized.

9. The apparatus of claim 8 wherein said means for controlling continues to simultaneously store said electrocardiographic signals in said first and second memories until the full capacity of said second memory is utilized provided that upon reading said time-of-day signal on and prior to full utilization of said capacity of said second memory said means for controlling discards stored electrocardiographic signals stored in said second memory after a second predetermined fraction of said capacity of said second memory is utilized and discards a selected portion of said stored electrocardiographic signals simultaneously stored in said first memory, said selected portion discarded from said first memory corresponding to said electrocardiographic signals stored in said second memory between said first and second predetermined fractions of said capacity of said second memory.

10. The apparatus of claim 5 wherein said means for controlling simultaneously stores said electrocardiographic signals in said first and second memory if said stored electrocardiographic signals in said second memory exceed a first predetermined fraction of the capacity of said second memory and no time-of-day signal has been read.

11. The apparatus of claim 10 wherein said means for controlling discards selected portions of said simultaneously stored electrocardiographic signals in said first and second memories when said first and second memories are read and said stored electrocardiographic signals are connected to said printer/plotter, said selected portions of said simultaneously stored electrocardiographic signals in said first and second memories being discarded so that no portion of said simultaneously stored electrocardiographic signals will not be twice plotted by said printer/plotter.

12. The apparatus of claim 11 wherein said selective discarding of simultaneously stored electrocardiographic signals by said means for controlling is dependent on whether or not a time-of-day signal was read after said predetermined fraction of said second memory had been utilized.

13. The apparatus of claim 12 wherein said means for controlling stores said electrocardiographic signals in said first preselected portions of said first and second memories, if a time-of-day signal is read after said first predetermined fraction of said capacity of said second memory had been utilized and wherein second portions of said first and second memories are discarded if no time-of-day signal is read after said predetermined fraction of said second memory is utilized.

14. Apparatus for controlling the operation of a printer-plotter to produce at a high speed on a medium marks that are representative of electrocardiographic signals generated at a slower real time speed by a patient, then stored along with time of day signals in a storage device, the time of day signals being correlated with the electrocardiographic signals and representing the time of day at which the respective electrocardiographic signals were generated, the electrocardiographic signals and the time of day signals both being later retrieved from the storage device, said apparatus comprising:

formatting means adapted to receive both the retrieved electrocardiographic signals and the retrieved time of day signals and connected to the printer-plotter for controlling it to plot at the high speed successive segments of the electrocardiographic signals in successive rows juxtaposed along the medium to facilitate visual analysis of the electrocardiographic signals, and for controlling the printer-plotter to print alpha-numeric symbols adjacent predetermined rows of the plotted electrocardiographic signals to indicate the time of day corresponding to the respective said predetermined rows.

15. The apparatus of claim 14 wherein said formatting means control the printer-plotter to plot the successive rows so that they all extend to one side from a common line and to print the alpha-numeric symbols on the opposite side of the common line.

16. Apparatus for controlling the operation of a printer-plotter to produce at a high speed in a medium marks that are representative of electrocardiographic signals generated at a slower real time speed by a patient, then stored in a storage device and later retrieved from the storage device by a playback apparatus that generates a time of day signal that is correlated with the electrocardiographic signals and that represents the time of day at which the respective electrocardiographic signals were generated, said apparatus comprising:

formatting means connected to the playback apparatus for receiving both the retrieved electrocardiographic signals and the time of day signals generated by the playback apparatus and connected to the printer-plotter for controlling it to plot at the high speed successive segments of the electrocardiographic signals in successive rows juxtaposed along the medium to facilitate visual analysis of the electrocardiographic signals, and for controlling the printer-plotter to print alpha-numeric symbols adjacent predetermined rows of the plotted electrocardiographic signals to indicate the time of day corresponding to the respective said predetermined rows.

17. The apparatus of claim 16 wherein said formatting means control the printer-plotter to plot the successive rows so that they all extend to one side from a common line and to print the alpha-numeric symbols on the opposite side of the common line.

18. A method for facilitating the visual analysis of an electrocardiographic signal generated at a real time rate in a patient and subsequently plotted as marks on a medium in relationship to a time-of-day signal, said method comprising the steps of:
(a) selectively storing the electrocardiographic signal as fast as it is generated in a first and second memory, said electrocardiographic signal being simultaneously stored in said first and second memories in a manner dependent on time of receipt of said time-of-day signal;
(b) storing said time-of-day signal correlated with the electrocardiographic signal and representing the time of day at which the electrocardiographic signal was generated; then later,
(c) reading the stored electrocardiographic signal and the stored time-of-day signal from said first and second memories, said electrocardiographic signal being read from said first and second memories dependent on time of receipt of said time-of-day signal;
(d) plotting at a speed greater than the real time speed successive segments of the read electrocardiographic signal stored prior to said time-of-day signal in successive rows juxtaposed along the medium; and
(e) printing alpha numeric symbols adjacent predetermined rows of the plotted electrocardiograph signals to indicate the time of day corresponding to each of said predetermined rows.

19. The method of claim 18, wherein in step (c) the stored electrocardiographic signal and the stored time of day signal are retrieved at a speed greater than the real time speed.

20. The method of claim 18, wherein step (d) the successive rows are plotted to extend to one side from a common line and wherein in step (e) the alpha-numeric symbols are printed on the opposite side of the common line.

21. A method for facilitating the visual analysis of ECG signals generated at a real time rate in a patient, recorded and subsequently plotted as lines of graphic data on a medium, said method comprising the steps of:
storing said ECG signals in a first memory until sufficient has been stored therein corresponding to a full line of graphic data on said medium;
next storing subsequent ECG signals in a second memory corresponding to a second adjacent line of graphic data on said medium;
reading and printing said ECG signals stored in said first memory as said graphic data on said medium as said ECG signals are being stored in said second memory;
where in said step of storing said ECG signals in said second memory, said signals are stored therein until a time-of-day signal is detected, provided that said time-of-day signal is detected prior to a predetermined fraction of the capacity of said second memory having been utilized; and
then simultaneously storing said ECG signals in said first and second memories, if said predetermined fraction of said capacity of said second memory has been utilized without detection of said time-of-day signal.

22. The method of claim 21 further comprising the steps of:
reading and printing a first selected portion of said ECG signals as said graphic data on said medium from said second memory, said first selected portion of said ECG signals being simultaneously stored within said first and second memories after said predetermined fraction of said second memory has been utilized and prior to detection of said time-of-day signal;
reading and printing said time of day signal on said medium at a selected position adjacent to said graphic data; and
then reading and printing a second selected portion of said ECG signals as said graphic data on said medium, said second selected portion of said ECG signals being simultaneously stored in said first memory subsequent to detection of said time-of-day signal.

23. The method of claim 21 further comprising the steps of:
reading and printing said ECG data stored in said second memory within said predetermined fraction of said memory if no time-of-day signal is detected; and
reading and printing said simultaneously stored ECG data in said first memory if no time-of-day signal is detected.

* * * * *